United States Patent [19]
Hsieh

[11] Patent Number: 5,833,594
[45] Date of Patent: Nov. 10, 1998

[54] MAGNETIC BRASSIERE

[76] Inventor: Chih-Ching Hsieh, No. 64, Lane 107, Lientsun Rd., Fengyuan City, Taichung Hsien, Taiwan

[21] Appl. No.: 796,222

[22] Filed: Feb. 7, 1997

[51] Int. Cl.[6] .................................................. A61N 1/00
[52] U.S. Cl. .................................. 600/15; 450/1; 450/78
[58] Field of Search .................................. 600/975; 2/73, 2/400, 406; 450/1, 78

[56] References Cited

U.S. PATENT DOCUMENTS 499,681  6/1893  Renstrom ................................. 600/13

FOREIGN PATENT DOCUMENTS 3719084  1/1988  Germany ................................. 600/15
0002878  7/1879  United Kingdom ..................... 600/9

Primary Examiner—John P. Lacyk
Attorney, Agent, or Firm—Watson Cole Grindle Watson, P.L.L.C.

[57] ABSTRACT

A brassiere includes two cups each having a first end portion connected with each other. Two side straps each have a first end extending outwardly from a second end portion of a corresponding one of the two cups. Two magnetic elements are each mounted on a second end of a corresponding one of the two side straps. At least one magnetic conducting wire extends through each of the two cups and through each of the two side straps and has two distal ends each connected to a corresponding one of the two magnetic elements.

1 Claim, 3 Drawing Sheets

MAGNETIC BRASSIERE

FIELD OF THE INVENTION

The present invention relates to a brassiere, and more particularly to a brassiere fitted with a magnetic material.

BACKGROUND OF THE INVENTION

A conventional brassiere is an undergarment worn by a woman for supporting and shaping her breasts only, and cannot provide other functions, thereby limiting the utility of the brassiere.

The present invention has arisen to mitigate and/or obviate the disadvantage of the conventional brassiere.

SUMMARY OF THE INVENTION

In accordance with one aspect of the present invention, there is provided a brassiere comprising two cups each having a first end portion connected with each other and a second end portion. Two side straps each have a first end extending outwardly from the second end portion of a corresponding one of the two cups and a second end.

Two magnetic elements are each mounted on the second end of a corresponding one of the two side straps.

At least one magnetic conducting wire extends through each of the two cups and through each of the two side straps and have two distal ends each connected to a corresponding one of the two magnetic elements.

Further features of the present invention will become apparent from a careful reading of the detailed description with appropriate reference to the accompanying drawings.

DETAILED DESCRIPTION OF THE PREFERRED EMBODIMENTS

Figure 1:
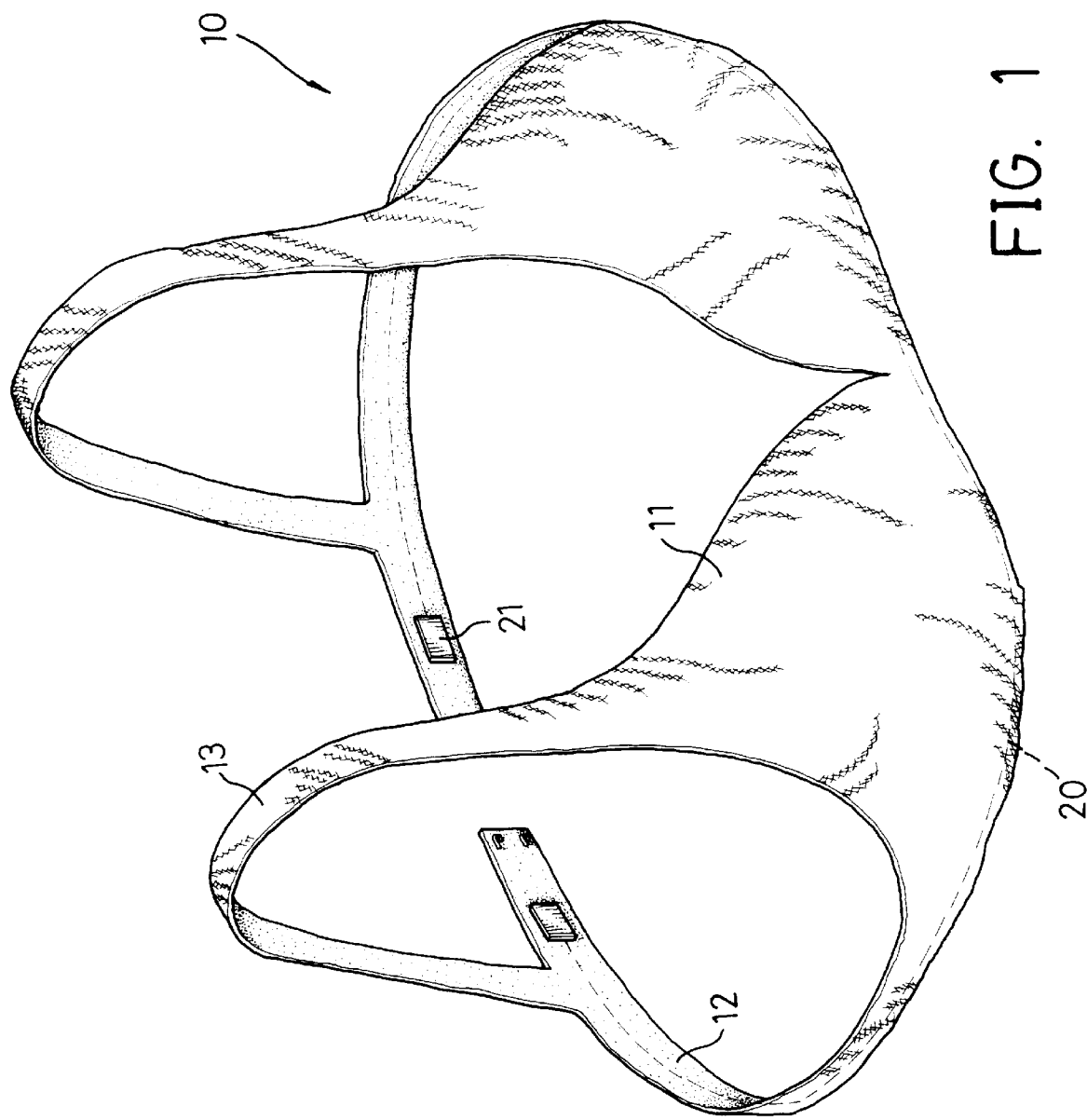
FIG. 1 is an perspective view of a brassiere in accordance with the present invention.
Figure 2:
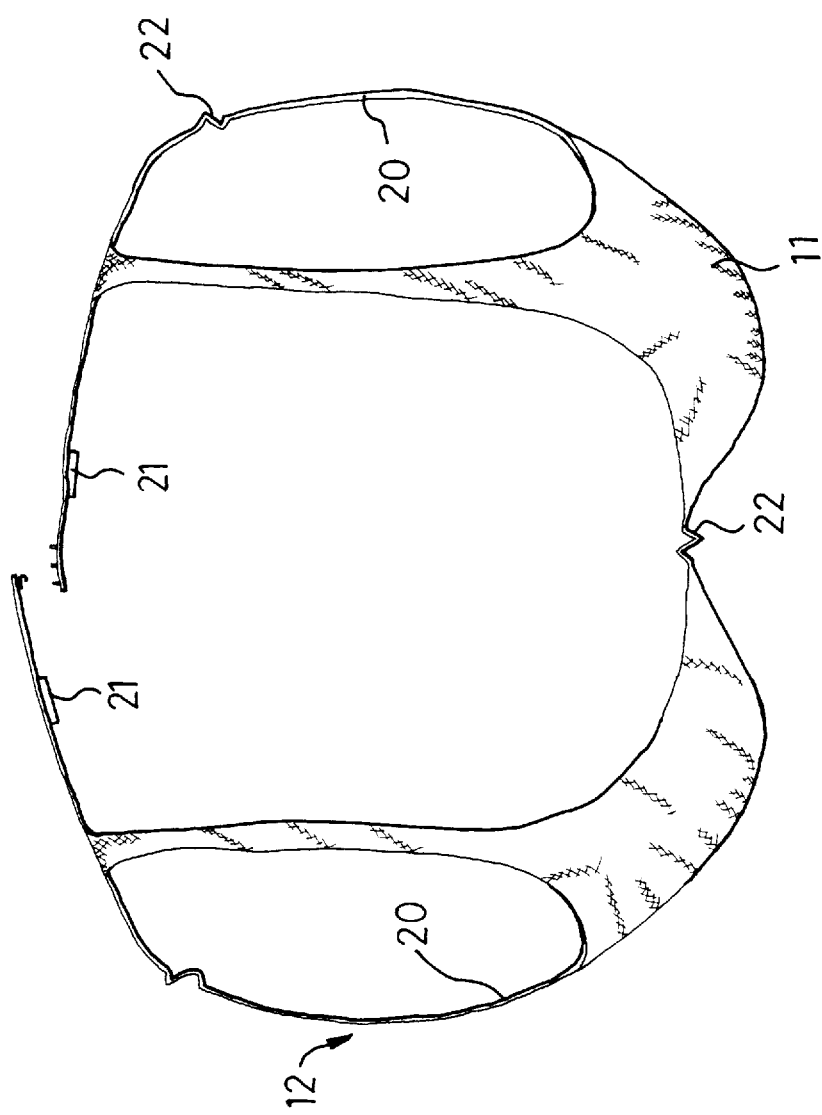
FIG. 2 is a top plan view of FIG. 1.
Figure 3:
FIG. 3 is a partially cross-sectional view showing a magnetic conducting wire being received in a side strap.

Referring to the drawings, and initially to FIGS. 1–3, a brassiere 10 in accordance with the present invention comprises two cups 11 each including a first end portion connected with each other and a second end portion.

Two side straps 12 each have a first end extending outwardly from the second end portion of a corresponding one of the two cups 11 and a second end. Two shoulder straps 13 each have a first end attached to a respective one of the two cups 11 and a second end attached to a respective one of the two side straps 12.

Two magnetic elements 21 are each mounted on the second end of a corresponding one of the two side straps 12. At least one magnetic conducting wire 20 extends through each of the two cups 11 and through each of the two side strap 12 and has two distal ends each connected to a corresponding one of the two magnetic elements 21.

The magnetic conducting wire 20 is made of a magnetic material and inherently gives off a magnetic field in the same manner as the two magnetic elements 21.

Especially referring to FIG. 2, the magnetic conducting wire 20 can be formed with a plurality of folding portions 22 for adjusting the dimensions of the brassiere 10 such that the brassiere 10 can be suitable for users of different sizes of chest measurement.

Figure 4:
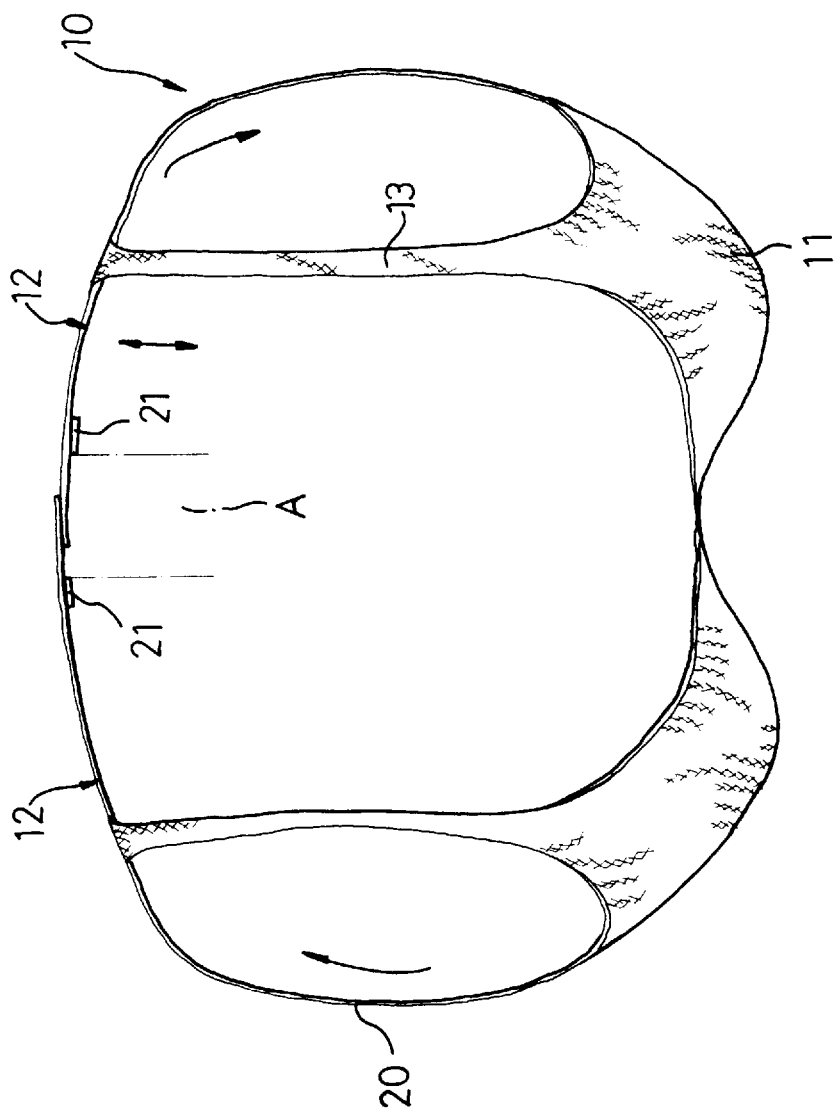
FIG. 4 is a top plan operational view of FIG. 1.

Referring to FIG. 4, the two side straps 12 can be connected with each other, with each of the two magnetic elements 21 located adjacent to a back region A of a user, and with the magnetic conducting wire 20 encompassing the upper body of the user, thereby promoting the user's blood circulation by means of the magnetic action of the two magnetic elements 21 and the magnetic conducting wire 20 so as to increase the user's health.

It should be clear to those skilled in the art that further embodiments may be made without departing from the scope and spirit of the present invention.

What is claimed is:

1. A brassiere comprising two cups each having a first end portion connected with each other and a second end portion, two side straps each having a first end extending outwardly from the second end portion of a corresponding one of said two cups and a second end, two magnetic elements each mounted on the second end of a corresponding one of said two side straps, and at least one magnetic conducting wire extending through each of said two cups and through each of said two side straps and having two distal ends each connected to a corresponding one of said two magnetic elements, wherein said magnetic conducting wire is formed with at least one folding portion for adjusting the dimensions of said brassiere such that said brassiere can be adapted for users of different sizes of chest measurement.

\* \* \* \* \*